US006458796B1

(12) United States Patent
Haning et al.

(10) Patent No.: US 6,458,796 B1
(45) Date of Patent: Oct. 1, 2002

(54) DIHYDRO-[1,2,3]TRIAZOLO-[4,5-D] PYRIMIDIN-7-ONE

(75) Inventors: Helmut Haning, Wuppertal (DE); Ulrich Niewöhner, Wermelskirchen (DE); Ulrich Rosentreter, Wuppertal (DE); Thomas Schenke, Bergisch Gladbach (DE); Erwin Bischoff, Wuppertal (DE); Karl-Heinz Schlemmer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/763,808

(22) PCT Filed: Aug. 13, 1999

(86) PCT No.: PCT/EP99/05955

§ 371 (c)(1),
(2), (4) Date: Feb. 26, 2001

(87) PCT Pub. No.: WO00/12504

PCT Pub. Date: Mar. 9, 2000

(30) Foreign Application Priority Data

Aug. 26, 1998 (DE) .......................................... 198 38 705

(51) Int. Cl.$^7$ .................... C07D 487/04; A61K 31/519; A61P 7/02
(52) U.S. Cl. ........................................ 514/258; 544/254
(58) Field of Search ........................... 544/254; 514/258

(56) References Cited

U.S. PATENT DOCUMENTS

| 4,076,711 A | 2/1978 | Ganguly et al. ...... 260/256.4 F |
| 5,861,396 A | 1/1999 | Niewöhner et al. ...... 514/234.2 |

FOREIGN PATENT DOCUMENTS

| EP | 0229011 | 7/1987 |
| EP | 0288431 | 10/1988 |
| EP | 0771799 | 5/1997 |
| GB | 1338235 | 11/1973 |
| WO | 9628429 | 9/1996 |

OTHER PUBLICATIONS

Albert, A., Trottar, A.M., "v–Triazolo[4,5–d]pyrimidines(8–Azapurines). Part 21. Synthesis of 2-Substituted 8–Azapurin–6–ones from 4–Amino–1,2,3–triazole–5–carb–oxamides and Amidines", J.C.S. Perkin I, pp. 922–925 (1979).

Barclay, G. A., Nyholm, R. S., and Parish, R. V., "Tritertiary Arsine Complexes of Nickel, Palladium, and Platinum", J. Chem. Soc., pp. 4433–4442 (1961).

Barili, P. L., "A Method for the Synthesis of Racemic and Optically Active 2–Substituted 9–(2', 3'–Dihydroxypropyl)–8–azabypoxanthines and 8–azaadenines [1]", J. Heterocyclic Chem., 28: 1351–1355 (1991).

Barili, P. L., Biagi, G., Livi, O., and Scartoni, V., "A Facile "One Pot" Synthesis of 2,9–Disubstituted–8–Azapurin–6–ones (3,5–Disubstituted 7–Hydroxy–3H–1,2,3–triazolo[4,5–d]pyrimidines", J. Heterocyclic Chem., 22: 1607–1609 (1985).

Beauchamp, L. M., Tuttle, J. V., Rodriguez, M. E., and Sznaidman, M. L., "Guanine, Pyrazolo[3,4–d]pyrimidine, and Triazolo[4,5–d]pyrimidine (8–Azaguanine) Phosphonate Acyclic Derivatives as Inhibitors of Purine Nucleoside Phosphorylase", J. Med. Chem., 39: 949–956 (1996).

Beavo, J. A., and Reifsnyder, D. H., "Primary Sequence of Cyclic Nucleotide Phosphodesterase Isozymes and the Design of Selective Inhibitors", TIPS, 11: 150155 (Apr. 1990).

Biagi, G., Giorgi, I., Livi, O., and Scartoni, V., "N(9)–Substituted 2–Phenyl–N(6)–Benzyl–8–Azaadenines. A1 Adenosine Receptor Affinity. A Comparison with the Corresponding N(6)–Substituted 2–Phenyl–N(9)–Benzyl–8–Azaadenines", Il Farmaco, 51(6): 395–399 (1996).

Biagi, G., Giorgi, I., Livi, O., and Scartoni, V., "Synthesis of New N(6)–Substituted 2–Phenyl–8–Azaadenosines. Their Affinity for Adenosine $A_1$ and $A_2$ Receptors. A Comparison with the Corresponding 2–Phenyl–9–Benzyl–8–Azaadenines. VI", Il Farmaco, 50(1): 13–19 (1995).

Biagi, G., Giorgi, I., Livi, O., and Scartoni, V., "N(6) or N(9) Substituted 2–Phenyl–8–Azadennines: Affinity for $A_1$ Adenosine Receptors. VII", Il Farmaco, 50(10):659–667 (1995).

Biagi, G., Giorgi, I., Livi, O., and Scartoni, V., "N(6)–Substituted 2–N–Butyl–9–Benzyl–8–Azaadenines. Affinity for Adenosine $A_1$ and $A_2$ Receptors. A Comparison with 2–N–Butyl Analogous Derivatives. IV", Il Farmaco, 49(3): 183–186 (1994).

Biagi, G., Giorgi, I., Livi, O., and Scartoni, V., "N(6)–Substituted–2–Phenyl–9–Benzyl–8–Azaadenines. Affinity for Adenosine $A_1$ and $A_2$ Receptors. A Comparison with 2–N–Butyl Analogous Derivatives. V", Il Farmaco, 49(3): 187–191 (1994).

Biagi, G., Giorgi, I., Livi, O., and Scartoni, V., "Synthesis of New 2 Substituted 9–β–D–Ribofuranosyl–8–Azahypoxanthines. VII", Il Farmaco, 47(5): 525–536 (1992).

Biagi, G., Giorgi, I., Livi, O., and Scartoni, V., "Evaluation of the Quantitative Contribution of an Aryl Group on C(2) of 8–Azaadenines to Binding with Adenosine Deaminase: A New Synthesis of 8–Azaadenosine. XI", Il Farmaco, 47(12): 1457–1476 (1992).

(List continued on next page.)

Primary Examiner—Mukund J. Shah
Assistant Examiner—Venkataraman Balasubramanian
(74) Attorney, Agent, or Firm—Jerrie L. Chiu

(57) ABSTRACT

The present invention relates to novel dihydro-[1,2,3]triazolo-[4,5-d]pyrimidin-7-one, to processes for their preparation and to their use as medicaments, in particular as inhibitors of cGMP-metabolizing phosphodiesterases.

10 Claims, No Drawings

OTHER PUBLICATIONS

Biagi, G., Franchi, M., Giorgi, I., Livi, O., and Scartoni, V., "One Pot Synthesis of 2-Substituted 9-(2'-Hydroxy-3'-aminopropyl)-8-azahypoxanthines and 8-azaadenines (5-Substituted-3-(2'-Hydroxy-3'-aminopropyl) 7-amino and 7-hydroxy-3H-1,2,3-triazolo[4,5-d]pyrimidines)", J. Heterocyclic Chem., 26: 39–43 (1989).

Broughton, B. J., Chaplen, P., Knowles, P., Lunt, E., Marshall, S. M., Pain, D. L., and Wooldridge, K. R. H., "Antiallergic Activity of 2-Phenyl-8-azapurin-6-ones", J. Med. Chem., 18(11): 1117–1122 (1975).

Holland, A., and Jackson, D., "Antiallergic Activity of 8-Azapurin-6-ones with Heterocyclic 2-Substituents", Eur. J. Med. Chem., Chimica Therapeutica, 10(5): 447–490 (1975).

Hoover, J. R. E., and Day, A. R., "Metabolite Analogs. VI. Preparation of Some Analogs of 4-Amino-5-imidazole-carboxamide", J. Chem. Soc. 78: 5832–5836 (1956).

Karanov, E., Alexieva, V., Glolovinsky, E., and Haimova, M., "Cytokinin and Anticytokinin Activity of Some-4-Substituted 1H-pyrazoles and 8-aza Analogues of Adenine", Plant Growth Regulation, 13: 7–11 (1993).

Lemay, H. E., and Hodgson, D. J., "Antiallergenic-8-Azapurines. Structural Characterization of 9-Diethylcarbamoyl-2-(2-propoxyphenyl)-8- azahypoxanthine", J. Am. Che. Soc., 100(2): 6474–6478 (1978).

Miyashita, A., Fujimoto, K., Okada, T., and Higashino, T., "Synthesis of Fused Pyrimidinones by Reaction of Aminoarenecarboxamide with Esters: Preparation of Pyrrolo[2,3-d]-, Thieno[2,3-d]-, Isoxazolo[5,4-d], and 1,2,3-Triazolo[4,5-d]Pyrimidinones, and Quinzolones", Heterocycles, 42(2): 691–699 (1996).

Nielsen, F. E., Pedersen, R. B., and Begtrup, M., "Synthesis of 8-Azapurin-6-ones and 8-Azapurin-6-imines from Etnyl 5-Acetylamino-1,2,3-triazole-4-carboxylates" Liebigs Ann. Chem., pp. 1848–1859 (1984).

Ried, W., and Laoutidis, J., "Synthese neuer stickstoffreicher Heterocyclen", Chemiker-Zeitung, 114(7/8):246–248 (1990).

Shealy, Y. F., O'Dell, C. A., and Arnett, G., "Synthesis and Antiviral Evaluation of Carbocyclic Analogues of 2-Amino-6-Substituted-purine 3-Deoxyribofuranosides", J. Med. Chem., 30: 1090–1094 (1987).

Shealy, Y. F., O'Dell, C. A., Shannon, W. M., and Arnett, G., "Synthesis and Antiviral Activity of Carbocyclic Analogues of 2-Deoxyribofuranosides of 2-Amino-6-substituted-purines and of 2-Amino-6-Substituted-8-azapurines", J. Med. Chem., 27: 1416–1421 (1984).

Stoclet, J.-C., Keravis, T., Komas, N., and Lugnier, C., "Cyclic Nucleotide Phosphodiesterases as Therapeutic Targets in Cardiovascular Diseases", Exp. Opin. Invest. Drugs, 4(11): 1081–1100 (1995).

Sutherland, D.R., and Tennant, G., "The Chemistry of Polyazaheterocyclic Compounds. Part IV. Dimroth Rearrangements of 4-Substituted-5-Amino-1-phenyl-1,2,3-triazoles and a Synthesis of v-Triazolo[4,5-d]pyrimidines", J. Chem. Soc. (C): 706–713 (1971).

Sznaidman, M. L., and Beauchamp, L. M., "Regioselective Synthesis of 9-Substituted-8-azaguanines (5-Amino-3-substituted-3,6-dihydro-7H-1,2,3-triazolo[4,5-d]pyrimidin-7-one)", J. Heterocyclic Chem., 33: 1605–1610 (1996).

DIHYDRO-[1,2,3]TRIAZOLO-[4,5-D]PYRIMIDIN-7-ONE

The present invention relates to novel dihydro-[1,2,3]triazolo-[4,5-d]pyrimidin-7-one, to processes for their preparation and to their use as medicaments, in particular as inhibitors of cGMP-metabolizing phosphodiesterases.

The synthesis of triazolopyrimidines has been described in J. Chem. Soc., C, 1971, 706. Fungicidal properties of dihydrotriazolopyrimidinones and their synthesis have been described in Liebigs Ann. 1984, 1848, by Nielsen et. al.

The synthesis of dihydrotriazolpyrimidinones by cyclization of an ester with an aminotriazolocarbonamide in the presence of a base has been described in J. Het. Chem. 1985, 22, 1607 by Biagi et al. and in Het. 1996, 42, 691 by Miyashita et al.; the analogous synthesis starting from amidines can be found in J. Chem. Soc., Perkin Trans. 1, 1979, 922.

Antiallergic properties of 1-unsubstituted dihydrotriazolopyrimidinones have been described in Eur. J. Med. Chem. 1975, 447, in J. Med. Chem. 1975, 1117 and in J. Am. Chem. Soc. 1978, 100, 6474. The synthesis of 5-amino-dihydrotriazolopyrimidinones has been described in J. Chem. Soc. 1961, 4433, and their antiviral activity has been reported in J. Med. Chem. 1987, 30, 1091 and J. Med. Chem. 1984, 27, 1416.

Anticytokine properties of 8-azaadenines are reported by Karanov et al. in Plant Growth Regul. 1993, 13, 7.

A synthesis method for azahypoxanthines and azaadenines is described by Biagi et al in J. Het. Chem. 1991, 28, 1351 and J. Het. Chem. 1989, 26, 39.

Anticonvulsive properties of 5-amino-dihydrotriazolopyrimidinones have been described in EP-288 431. Furthermore, the synthesis of 5-amino-dihydrotriazolopyrimidinones is described in J. Het. Chem. 1996, 33, 1605. Adenosine A1 receptor affinity of azaadenines and binding to adenosine deaminase has been reported in Farmaco 1996, 51, 395, Farmaco 1995, 50, 659 and Farmaco 1994, 49, 187.

Purine-nucleoside phosphorylase-inhibitory properties of azaguanines are described in J. Med. Chem. 1996, 39, 949.

Syntheses of dihydrotriazolopyrimidinones are furthermore found in Farmaco 1995, 50, 13, Farmaco 1994, 49, 183, Farmaco 1992, 47, 1457, Farmaco 1992, 47, 525 and in Chem. Ztg. 1990, 114, 246.

The synthesis of intermediates of the type II has been described in EP 0 229 011 and in J. Chem. Soc. 78, 1956, 5832.

Triazolopyrimidinones of the general formula (I) having the stated substitution pattern R$_1$, A, D and L are novel.

The compounds according to the invention are potent inhibitors of either one or more of the phosphodiesterases which metabolize cyclic guanosine 3',5'-monophophate (cGMP PDE's). According to the nomenclature of Beavo and Reifsnyder (Trends in Pharmacol. Sci. 11, 150–155, 1990), these are the phosphodiesterase isoenzymes PDE-I, PDE-II and PDE-V.

An increase in the cGMP concentration can lead to beneficial antiaggregatory, antithrombotic, antiprolific, antivasospastic, vasodilative, natriuretic and diuretic effects. It can influence the short- or long-term modulation of vascular and cardiac inotropy, the pulse and cardiac conduction (J. C. Stoclet, T. Keravis, N. Komas and C. Kugnier, Exp. Opin. Invest. Drugs (1995), 4 (11), 1081–1100).

The present invention relates to dihydro-[1,2,3]triazolo-[4,5-d]pyrimidin-7-ones of the general formula (I)

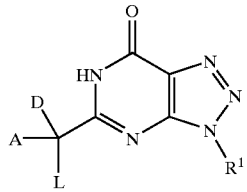

in which
R$^1$ represents cycloalkyl having 3 to 8 carbon atoms, or represents a radical of the formula

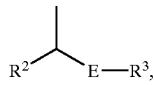

in which
R$^2$ represents straight-chain or branched alkyl having up to 10 carbon atoms which is optionally substituted by hydroxyl,
E represents a radical of the formula —CH$_2$—T,
in which
T represents a straight-chain or branched alkylene chain having up to 10 carbon atoms,
R$^3$ represents hydrogen or aryl having 6 to 10 carbon atoms which is optionally substituted up to 3 times by identical or different substitutents from the group consisting of halogen, hydroxyl, nitro, trifluoromethyl and straight-chain or branched alkyl or alkoxy having in each case up to 6 carbon atoms,
A and D represent hydrogen,
or
A represents hydrogen
and
D represents hydroxyl,
or
A and D together represent a radical of the formula =O,
L represents a radical of the formula

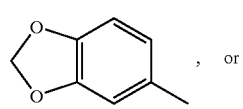, or represents aryl having 6 to 10 carbon atoms or represents a 5- to 7-membered aromatic, optionally benzo-fused heterocycle having up to 3 heteroatoms from the group consisting of S, N and/or O, where the ring systems listed above under L are substituted up to 3 times by one or more identical or different of the following substituents: halogen, hydroxyl, nitro, trifluoromethyl, carboxyl, straight-chain or branched alkyl, alkoxy and alkoxycarbonyl having in each case up to 6 carbon atoms, a radical of the formula —(V)$_a$—NR$^4$R$^5$,
in which
a represents a number 0 or 1,
V represents a radical of the formula —CO or —SO$_2$,
R$^4$ and R$^5$ are identical or different and represent hydrogen or straight-chain or branched acyl or alkoxycarbonyl having in each case up to 6 carbon atoms, or represent straight-chain or branched alkyl having up to 6 carbon atoms which is optionally substituted by hydroxyl, amino or by straight-chain or branched alkyl- or dialkylamino having in each case up to 6 carbon atoms, or R⁴ and R⁵ together with the nitrogen atom form a 5- or 6-membered saturated heterocycle which may optionally contain a further heteroatom from the group consisting of S and O or a radical of the formula —NR⁶ and which is optionally substituted by straight-chain or branched alkoxycarbonyl having up to 6 carbon atoms,
in which
R⁶ represents hydrogen or straight-chain or branched alkyl having up to 4 carbon atoms,
and/or the ring systems listed under L are optionally substituted by aryl having 6 to 10 carbon atoms and a 5- to 7-membered aromatic, optionally benzo-fused heterocycle having up to 3 heteroatoms from the group consisting of S, N and O, where these ring systems for their part are optionally substituted up to 2 times by identical or different substituents from the group consisting of halogen, hydroxyl, nitro, carboxyl, trifluoromethyl and straight-chain or branched alkyl, alkoxy, or alkoxycarbonyl having in each case up to 5 carbon atoms, or by a group of the formula —(V')$_b$—NR⁷R⁸,
in which
b has the meaning of a given above and is identical to or different from this meaning,
R⁷ and R⁸ have the meanings of R⁴ and R⁵ given above and are identical to or different from these meanings,
V' has the meaning of V given above and is identical to or different from this meaning,
and their tautomers and salts.

The substances according to the invention can also be present as salts. In the context of the invention, preference is given to physiologically acceptable salts.

Physiologically acceptable salts can be salts of the compounds according to the invention with inorganic or organic acids. Preference is given to s alts with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid, or naphthalenedisulphonic acid.

Physiologically acceptable salts can also be metal or ammonium salts of the compounds according to the invention. Particular preference is given, for example, to sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds of the general formula (I) according to the invention can be present in various stereochemical forms which are either like image and mirror image (enantiomers) or which are not like image and mirror image (diastereomers). The invention relates both to the different stereoisomers and to the racemic forms and the diastereomer mixtures. The racemic forms, like the diastereomers, can be separated into the stereoisomerically uniform components in a known manner.

In the context of the invention, cycloalkyl having 3 to 8 carbon atoms represents cyclopropyl, cyclopentyl, cyclobutyl, cyclohexyl, cycloheptyl or cyclooctyl. The following may be mentioned as being preferred: cyclopropyl, cyclopentyl and cyclohexyl.

Aryl having 6 to 10 carbon atoms generally represents an aromatic radical having 6 to 10 carbon atoms. Preferred aryl radicals are phenyl and naphthyl.

In the context of the invention, alkyl having up to 6 carbon atoms represents a straight-chain or branched alkyl radical having 1 to 6 carbon atoms. Preference is given to a straight-chain or branched alkyl radical having 1 to 4 carbon atoms. Particular preference is given to a straight-chain or branched alkyl radical having 1 to 3 carbon atoms. The following may be mentioned by way of example: methyl, ethyl, n-propyl, isopropyl, tert-butyl, n-pentyl and n-hexyl.

In the context of the invention, alkoxy having up to 6 carbon atoms represents a straight-chain or branched alkoxy radical having 1 to 6 carbon atoms. Preference is given to a straight-chain or branched alkoxy radical having 1 to 4 carbon atoms. Particular preference is given to a straight-chain or branched alkoxy radical having 1 to 3 carbon atoms. The following may be mentioned by way of example: methoxy, ethoxy, n-propoxy, isopropoxy, tert-butoxy, n-pentoxy and n-hexoxy.

In the context of the invention, alkoxycarbonyl having up to 6 carbon atoms represents a straight-chain or branched alkoxycarbonyl radical having 1 to 6 carbon atoms.

Preference is given to a straight-chain or branched alkoxycarbonyl radical having 1 to 4 carbon atoms. Particular preference is given to a straight-chain or branched alkoxycarbonyl radical having 1 to 3 carbon atoms. The following may be mentioned by way of example: methoxycarbonyl, ethoxycarbonyl, n-propoxycarbonyl, iso-propoxycarbonyl and tert-butoxycarbonyl.

In the context of the invention, acyl having up to 6 carbon atoms represents a straight-chain or branched acyl radical having 1 to 6 carbon atoms. Preference is given to a straight-chain or branched acyl radical having 1 to 4 carbon atoms. Particular preference is given to a straight-chain or branched acyl radical having 1 to 3 carbon atoms. The following may be mentioned by way of example: acetoxy, ethylcarbonyl or n-propylcarbonyl.

In the context of the invention, heterocycle generally, depending on the substituent in question, represents an aromatic, optionally benzo-fused or unsaturated 5- to 7-membered, preferably 5- or 6-membered, heterocycle which may contain up to 3 heteroatoms from the group consisting of S, N and O, or represents a 5- or 6-membered saturated heterocycle which may optionally contain a further heteroatom from the group consisting of S and O. The following may be mentioned by way of example: pyridine, pyrimidyl, piperazinyl, thienyl, furyl, morpholinyl, pyrrolidinyl, piperazinyl or piperidyl. Preference is given to pyridine, thienyl, morpholinyl and piperidinyl.

In the context of the invention, halogen generally represents fluorine, chlorine, bromine and iodine. Preference is given to fluorine, chlorine and bromine. Particular preference is given to fluorine and chlorine.

Preference is given to compounds of the general formula (I),
in which
R¹ represents cyclopropyl, cyclobutyl, cyclopentyl, cyclohexyl or cycloheptyl, or represents a radical of the formula

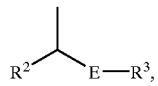

in which
R² represents straight-chain or branched alkyl having up to 8 carbon atoms which is optionally substituted by hydroxyl,
and E represents a radical of the formula —CH$_2$—T—,
in which
T represents a straight-chain or branched alkylene chain having up to 8 carbon atoms,
R$^3$ represents hydrogen or phenyl which is optionally substituted up to 2 times by identical or different substituents from the group consisting of fluorine, chlorine, bromine, hydroxyl, nitro, trifluoromethyl and straight-chain or branched alkyl or alkoxy having in each case up to 5 carbon atoms, A and D represent hydrogen,
or
A represents hydrogen
and
D represents hydroxyl,
or
A and D together represent a radical of the formula =O,
L represents a radical of the formula

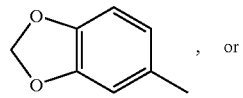, or represents phenyl, naphthyl, pyridyl, thienyl, indolyl or furyl, which are optionally substituted up to 3 times by identical or different substituents selected from the group consisting of fluorine, chlorine, bromine, trifluoromethyl, hydroxyl, nitro, carboxyl, straight-chain or branched alkyl, alkoxy and alkoxycarbonyl having in each case up to 5 carbon atoms and/or by a radical of the formula —(V)$_a$NR$^4$R$^5$,
in which
a represents a number 0 or 1,
V represents a radical of the formula —CO or —SO$_2$,
R$^4$ and R$^5$ are identical or different and represent hydrogen or straight-chain or branched acyl or alkoxycarbonyl having in each case up to 4 carbon atoms, or
represent straight-chain or branched alkyl having in each case up to 5 carbon atoms which is optionally substituted by hydroxyl, amino or by straight-chain or branced alkyl- or dialkylamino having in each case up to 5 carbon atoms,
or
R$^4$ and R$^5$ together with the nitrogen atom form a morpholinyl, piperidinyl or piperazinyl ring which is optionally substituted via a nitrogen atom by straight-chain or branched alkyl having up to 3 carbon atoms, which rings are optionally substituted by straight-chain or branched alkoxycarbonyl having up to 4 carbon atoms,
and/or the ring systems listed under L are optionally substituted by naphthyl, phenyl, pyridyl, indolyl, thienyl and furyl which are optionally substituted by fluorine, chlorine, bromine, hydroxyl, nitro, carboxyl, trifluoromethyl or by straight-chain or branched alkyl, alkoxy or alkoxycarbonyl having in each case up to 3 carbon atoms or by a group of the formula —(V')$_b$NR$^7$R$^8$,
in which
b has the meaning of a given above and is identical to or different from this meaning,
V' has the meaning of V given above and is identical to or different from this meaning, R$^7$ and R$^8$ have the meanings of R$^4$ and R$^5$ given above,
and their tautomers and salts.

Particular preference is given to compounds of the general formula (I)
in which
R$^1$ represents cyclopropyl, cyclobutyl, cyclopentyl, cyclohexyl or cycloheptyl, or represents a radical of the formula

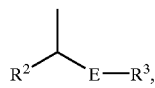

in which
R$^2$ represents straight-chain or branched alkyl having up to 7 carbon atoms which is optionally substituted by hydroxyl,
and
E represents a radical of the formula —CH$_2$—T—,
in which
T represents a straight-chain or branched alkylene chain having up to 7 carbon atoms,
R$^3$ represents hydrogen or phenyl which is optionally substituted up to 2 times by identical or different substituents from the group consisting of fluorine, chlorine, bromine, hydroxyl, nitro, trifluoromethyl and straight-chain or branched alkyl or alkoxy having in each case up to 4 carbon atoms,
A and D represent hydrogen,
or
A represents hydrogen
and
D represents hydroxyl,
or
A and D together represent a radical of the formula =O,
L represents a radical of the formula

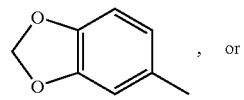, or represents phenyl or pyridyl which are optionally substituted up to 3 times by identical or different substituents selected from the group consisting of fluorine, chlorine, bromine, trifluoromethyl, hydroxyl, nitro, carboxyl, straight-chain or branched alkyl, alkoxy and alkoxycarbonyl having in each case up to 4 carbon atoms and/or by a radical of the formula —(V)$_a$NR$^4$R$^5$,
in which
a represents a number 0 or 1,
V represents a radical of the formula —CO or —SO$_2$,
R$^4$ and R$^5$ are identical or different and represent hydrogen or straight-chain or branched acyl or alkoxycarbonyl having in each case up to 3 carbon atoms, or
represent straight-chain or branched alkyl having in each case up to 4 carbon atoms which is optionally substituted by hydroxyl, amino or by straight-chain or branched alkyl- or dialkylamino having in each case up to 3 carbon atoms,
or
R$^4$ and R$^5$ together with the nitrogen atom form a morpholinyl, piperidinyl or piperazinyl ring which is optionally substituted via a nitrogen atom by straight-chain or branched alkyl having up to 3 carbon atoms, which rings are optionally substituted by straight-chain or branched alkoxycarbonyl having up to 4 carbon atoms, and/or the ring systems listed under L are optionally substituted by phenyl or pyridyl,
and their tautomers and salts.

Moreover, a process for preparing the compounds of the general formula (I) according to the invention has been found which is characterized in that
in the case where A, D=H, compounds of the general formula (II),

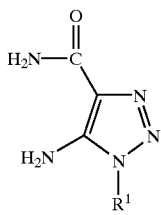
(II)

in which
R¹ is as defined above,
are reacted with compounds of the general formula (III)

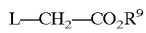
(III)

in which
L is as defined above
and
R⁹ represents $C_1$–$C_4$-alkyl,
in inert solvents, if appropriate in the presence of a base,
and the substituents listed under the substituents R¹, R³ and L are, if appropriate, introduced or derivatized by subsequent reactions such as acylation, oxidation, substitution and/or reductions.

The process according to the invention can be illustrated in an exemplary manner by the equation below:

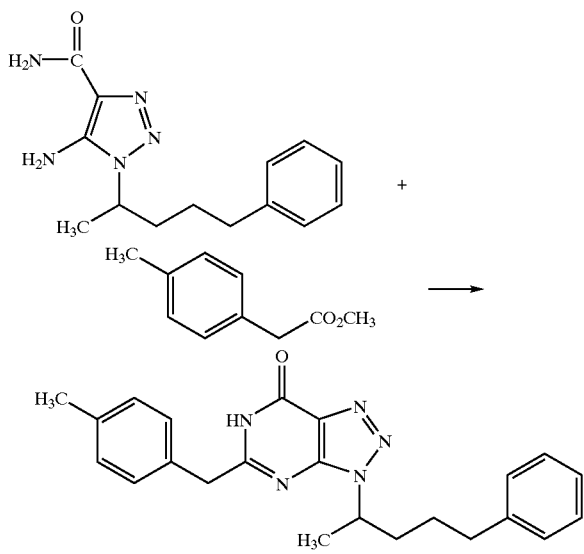

Solvents which are suitable for the process are the customary organic solvents. These preferably include alcohols, such as methanol, ethanol, propanol, isopropanol, butanol or t-butanol, or ethers, such as tetrahydrofuran or dioxane, or dimethylformamide or dimethyl sulphoxide. Particular preference is given to using alcohols, such as methanol, ethanol, propanol, isopropanol and acetonitrile and dimethylformamide. It is also possible to use mixtures of the solvents mentioned.

Bases which are suitable for the process are the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate, or alkali metal alkoxides, such as sodium methoxide, sodium ethoxide, potassium methoxide, potassium ethoxide or potassium tert-butoxide. Particular preference is given to sodium methoxide and sodium ethoxide.

When carrying out the process, the base is generally employed in an amount of from 2 to 6 mol, preferably from 3 to 5 mol, based on 1 mol of the corresponding amides.

The process is generally carried out at atmospheric pressure. However, it is also possible to carry out the process at elevated pressure or reduced pressure (for example in a range of from 0.5 to 5 bar).

The reaction with alkylsulphonyl chlorides is carried out, starting from the corresponding free hydroxyl compounds, in one of the abovementioned solvents and one of the bases, preferably using dichloromethane, triethylamine or pyridine, in a temperature range of from −20C to +20° C., preferably 0° C., and at atmospheric pressure.

The azide radical is generally introduced by reacting the corresponding alkylsulphonyloxy-substituted compounds with sodium azide in one of the solvents listed above, preferably dimethylformamide and dimethyl sulphonyl, in a temperature range of from 50° C. to +120° C., preferably 50° C., and at atmospheric pressure.

The enantiomerically pure compounds are obtainable by customary methods, for example by chromatography of the racemic compounds of the general formula (I) on chiral phases, or by using chiral starting materials.

Some of the compounds of the general formula (II) are known and some are novel and can be prepared, for example, by reacting compounds of the general formula (IV)

(IV)

in which
R¹ is as defined above
with compounds of the formula (V)

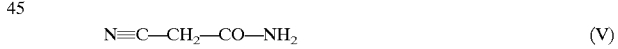
(V)

in inert solvents in the presence of a base.

Solvents which are suitable for the process are the customary organic solvents. These preferably include alcohols, such as methanol, ethanol, propanol, isopropanol, butanol or tert-butanol, or ethers, such as tetrahydrofuran or dioxane, or dimethylformamide or dimethyl sulphoxide. Particular preference is given to using alcohols, such as methanol, ethanol, propanol, isopropanol, and acetonitrile, dimethylformamide and dimethyl sulphoxide. It is also possible to use mixtures of the solvents mentioned.

Bases which are suitable for the process are the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate, or alkali metal alkoxides, such as sodium methoxide, sodium ethoxide, potassium methoxide, potassium ethoxide or potassium tert-butoxide. Particular preference is given to sodium methoxide and sodium ethoxide.

The process is generally carried out in a temperature range of from 0° C. to +180° C., preferably of from +20° C. to +150° C.

The process is generally carried out at atmospheric pressure. However, it is also possible to carry out the process at elevated pressure or reduced pressure (for example in the range of from 0.5 to 5 bar).

The compounds of the general formulae (IV) and (V) are known per se or can be prepared by customary methods.

The compounds of the general formula (I) according to the invention have an unforeseeable useful pharmacological activity spectrum.

They inhibit either one or more of the c-GMP-metabolizing phosphodiesterases (PDE I, PDE II and PDE V). This leads to an increase of c-GMP. The differentiated expression of the phosphodiesterases in different cells, tissues and organs, as well as the differentiated subcellular localization of these enzymes, in combination with the selective inhibitors according to the invention make it possible to selectively address the various cGMP-regulated processes.

Moreover, the compounds according to the invention enhance the activity of substances such as, for example, EDRF (endothelium derived relaxing factor), ANP (atrial natriuretic peptide), of nitrovasodilators and all other substances which increase the cGMP concentration in a manner different from that of phosphodiesterase inhibitors.

They can therefore be employed in medicaments for treating cardiovascular disorders, such as, for example, for treating hypertension, neuronal hypertension, stable and unstable angina, peripheral and cardiovascular disorders, arrhythrnias, for treating thromboembolic disorders and ischaemias such as myocardial infarction, stroke, transistory and ischaemic attacks, angina pectoris, obstruction of peripheral circulation, prevention of restenoses after thrombolysis therapy, percutaneous transluminal angioplasty (PTA), percutaneous transluminal coronary angioplasties (PTCA) and bypass. Furthermore, they may also be of significance for cerebrovascular disorders. Owing to their relaxing action on smooth muscles, they are suitable for treating disorders of the urogenital system such as hypertrophy of the prostate, incontinence and, in particular, for treating erectile dysfunction and female sexual dysfunction.

Activity of the Phosphordiesterases (PDEs)

The c-GMP-stimulated PDE II, the c-GMP-inhibited PDE III and the cAMP-specific PDE IV were isolated either from porcine or bovine heart myocardium. The $Ca^{2+}$-calmodulin-stimulated PDE I was isolated from porcine aorta, porcine brain or, preferably, from bovine aorta. The c-GMP-specific PDE V was obtained from porcine small intestine, porcine aorta, human platelets and, preferably, from bovine aorta. Purification was carried out by anion exchange chromatography over MonoQ$^R$ Pharmacia, essentially following the method of M. Hoey and Miles D. Houslay, Biochemical Pharmacology, Vol. 40, 193–202 (1990) and C. Lugman et al. Biochemical Pharmacology Vol. 35 1743–1751 (1986).

The enzyme activity is determined using a test mixture of 100 μl in 20 mM Tris/HCl buffer pH 7.5 containing 5 mM $MgCl_2$, 0.1 mg/ml of bovine serum albumin and either 800 Bq $^3$HcAMP or $^3$HcGMP. The final concentration of the nucleotides in question is $10^{-6}$ mol/l. The reaction is initiated by addition of the enzyme and the amount of enzyme is such that during the incubation time of 30 min, approximately 50% of the substrate is converted. To test the cGMP-stimulated PDE II, $^3$HcAMP is used as substrate and $10^{-6}$ mol/l of non-labelled cGMP are added to the mixture. To test the Ca-calmodulin-dependent PDE I, 1 μM of $CaCl_2$ and 0.1 μM of calmodulin are added to the reaction mixture. The reaction is quenched by addition of 100 μL of acetonitrile, containing 1 mM cAMP and 1 mM AMP. 100 μl of the reaction mixture are separated by HPLC and the cleavage products are determined quantitatively on-line using a continuous scintillation counter. The substance concentration measured is the concentration at which the reaction rate is reduced by 50%. Additionally, the "phodiesterase [$^3$H] cAMP-SPA enzyme assay" and the "phosphodiesterase [$^3$H] cGMP-SPA enzyme assay" from Amersham Life Science were used for testing. The test was carried out according to the test protocol of the manufacturer. To determine the activity of PDE2, the [$^3$H] cAMP-SPA assay was used, and $10^{-6}$ M cGMP were added to the reaction mixture to activate the enzyme. To measure PDE1, $10^{-7}$ M calmodulin and 1 μM $CaCl_2$ were added to the reaction mixture. PDE5 was measured using the [$^3$H] cGMP-SPA assay.

| Inhibition of the phosphodiesterases in vitro | | | |
|---|---|---|---|
| Ex. No. | PDE I IC50 [nM] | PDE II IC50 [nM] | PDE V IC50 [nM] |
| 5 | 500 | 80 | 500 |
| 19 | 200 | 200 | >1000 |
| 23 | 100 | 100 | >1000 |
| 30 | 500 | 300 | =1000 |
| 31 | >1000 | 40 | >1000 |

In principle, inhibition of one or more phosphodiesterases of this type results in an increase in the cGMP concentration. Thus, the compounds are of interest for all therapies in which an increase in the cGMP concentration is considered to be beneficial.

The cardiovascular effects were investigated using SH-rats and dogs. The substances were administered intravenously or orally.

The erection-stimulating action was investigated using rabbits which were awake [Naganuma H, Egashira T, Fuji J, Clinical and Experimental Pharmacology and Physiology 20, 177–183 (1993)]. The substances were administered intravenously, orally or parenterally.

The novel active compounds and their physiologically acceptable salts (for example hydrochlorides, maleates or lactates) can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, it optionally being possible, for example, to use organic solvents as auxiliary solvents if the diluent used is water.

Administration is carried out in a customary manner, preferably orally, transdermally or parenterally, for example perlingually , buccally, intravenously, nasally, rectally or inhalatively.

In spite of this, it may be necessary to depart from the amounts mentioned below, namely depending on the body weight or the type of administration route, on the individual response towards the medicament, the type of its formulation and the time or interval at which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

For human use, in the case of oral administration, it is good practice to administer doses of from 0.001 to 50 mg/kg, preferably 0.01 mg/kg–20 mg/kg. In the case of parenteral administration, it is good practice to use doses of from 0.001 mg/kg–0.5 mg/kg.

The compounds according to the invention are also suitable for use in veterinary medicine. For use in veterinary medicine, the compounds or their non-toxic salts can be administered in a suitable formulation in accordance with general veterinary practice. Depending on the kind of animal to be treated, the veterinary surgeon can determine the nature of use and the dosage.

STARTING MATERIALS

EXAMPLE I

5-Phenylpentan-2-ol

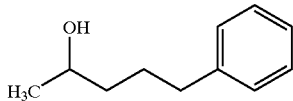

In one portion, 3.6 ml (4.72 g, 23.7 mmol) of 3-phenylpropyl bromide are added to a suspension of 5.2 g (213 mmol) of magnesium in 30 ml of diethyl ether. A further 30 ml (39.3 g, 197 mmol) of 3-phenylpropyl bromide are added dropwise at such a rate that constant reflux is maintained. After the addition has ended, the mixture is diluted with 100 ml of diethyl ether and refluxed for 30 min. The mixture is diluted with a further 80 ml of diethyl ether and cooled to −78° C. A solution, of a temperature of 0° C., of 19 ml of acetaldehyde in 50 ml of ether is added dropwise, and the reaction mixture is stirred at −78° C. for 2 hours and warmed to room temperature. 50 ml of saturated $NH_4Cl$ solution are added and the organic phase is extracted with 1N HCl and saturated $NaHCO_3$ solution and dried over $Na_2SO_4$. Removal of the solvent gives 33.4 g (95%) of a slightly yellow oil.

$R_f$=0.50 (petroleum ether/ethyl acetate=7:3).

EXAMPLE II

1-Methyl-4-phenylbutyl Methanesulphonate

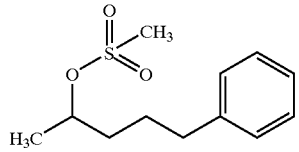

32.55 g of 5-phenylpentan-2-ol (198 mmol) are dissolved in 500 ml of pyridine and, at room temperature, admixed with 31 ml (45.88 g, 400 mmol) of mesyl chloride. The mixture is stirred at room temperature for 30 minutes and the solvent is then removed under reduced pressure and the residue is taken up in 200 ml of $CH_2Cl_2$. The mixture is extracted with 1N HCl and saturated $NaHCO_3$ solution, dried over $Na_2SO_4$ and concentrated using a rotary evaporator. This gives 54.01 g of a brown oil which still contains MesCl.

$R_f$=0.27 (cyclohexane/ethyl acetate=3:1).

EXAMPLE III (4-Azidopentyl)-benzene

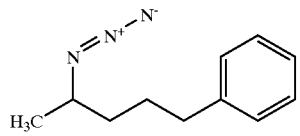

1.57 g of 1-methyl-4-phenylbutyl methanesulphonate (6.5 mmol) are dissolved in 30 ml of DMSO and the solution is admixed with 1.66 g $NaN_3$ (25.5 mmol) and stirred at 50° C. for 15 hours. The solution is diluted with 150 ml of ether and 100 ml of saturated aqueous $NaHCO_3$ solution, the organic phase is washed twice with water and dried over $Na_2SO_4$ and the solvent is removed under reduced pressure. This gives 997 mg (81%) of a yellow oil.

$R_f$=0.61 (cyclohexane/ethyl acetate=3:1).

EXAMPLE IV

5-Amino-1-(1-methyl-4-phenyl-butyl)-1H-[1,2,3]triazole-4-carboxamide

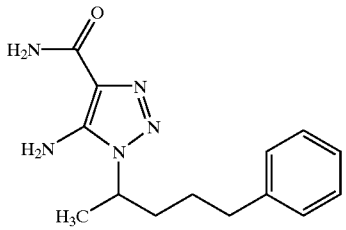

A solution of 997 mg (5.28 mmol) of (4-azidopentyl)-benzene and 672 mg (8 mmol) of cyanoacetamide in 3 ml of DMSO is admixed with a solution, of a temperature of 50° C., of 127 mg (5.5 mmol) of sodium in 3 ml of ethanol. The reaction mixture is stirred at room temperature for 15 h and then poured into 25 ml of ice-water. The pH is adjusted to pH 2 using 1N HCl and the precipitated solid is filtered off with suction, washed with water and dried under reduced pressure. This gives 1.14 g (79%) of a slightly yellow solid.

M.p.: 117° C.

EXAMPLE V AND EXAMPLE VI

Methyl (4-Chlorosulphonyl-phenyl)-acetate (Example V) and Methyl (3-Chlorosulphonyl-phenyl)-acetate (Example VI)

(Example V)

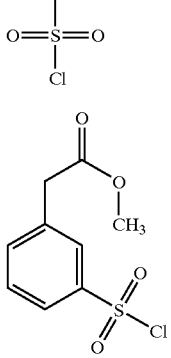

(Example VI)

288 ml (2 mol) of methyl phenylacetate are slowly added dropwise, with ice-cooling, to 400 ml (6 mol) of chlorosulphonic acid, and the reaction mixture is stirred at room temperature for 16 hours. The mixture is poured into 3 l of ice-water and extracted three times with ethyl acetate, and the organic phase is dried over sodium sulphate. Chromatographic purification (cyclohexane/ethyl acetate=3:1) gives 135.9 g (27.3%) of a yellow oil.

$R_f$=0.75 (cyclohexane/ethyl acetate=1:1).

The resulting product contains about 89% of the para and 11% of the meta regioisomer.

EXAMPLE VII

3-Nonanol

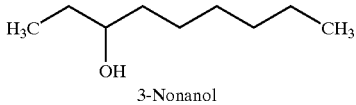

3-Nonanol 20.5 g (144 mmol) of 3-nonanone are initially charged in 200 ml of methanol, 5.45 g (144 mmol) of sodium borohydride are added a little at a time at room temperature and the mixture is stirred overnight. The solvent is removed under reduced pressure and the mixture is then acidified and extracted with dichloromethane. The organic phase is dried over sodium sulphate. Removal of the solvent gives 20 g (96%) of a colourless oil.

200 MHz-$^1$H-NMR (CDCl$_3$, ppm): 3.52, m, 1H; 1.48, m, 13H; 0.95, t, 3H; 0.89, t, 3H.

EXAMPLE VIII

1-Ethyl-heptyl Methanesulphonate

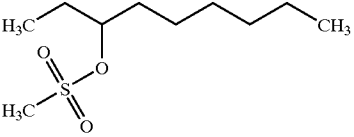

20 g (138.6 mmol) of 3-nonanol and 15.43 g of triethylamine are dissolved in 150 ml of dichloromethane and admixed dropwise with 17.47 g (152.5 mmol) of mesyl chloride. The mixture is stirred at room temperature for 4 hours. The organic phase is extracted twice with water and dried over sodium sulphate and the solvent is removed under reduced pressure. This gives 30.7 g (95%) of a yellow liquid.

200 MHz-$^1$H-NMR (CDCl$_3$, ppm): 4.67, quin., 1H; 3.00, s, 3H; 1.71, m, 4H; 1.30, m, 8H; 0.99, t, 3H; 0.90, t, 3H.

EXAMPLE IX

3-Azidononane

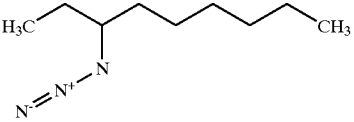

15.0 g (67.46 mmol) of 1-ethyl-heptyl methanesulphonate are dissolved in 300 ml of DMSO and, after addition of 17.54 g (269.8 mmol) of sodium azide, the mixture is stirred at 50° C. for 16 hours. The reaction mixture is poured into ice-water and extracted three times with ether. The extract is dried over sodium sulphate giving 11.4 g (96%) of a yellow liquid.

200 MHz-$^1$H-NMR (CDCl$_3$, ppm): 3.18, quin., 1H; 1.40, m, 12H; 0.99, t, 3H; 0.90, t, 3H.

EXAMPLE X

5-Amino-1-(1-methyl-heptyl)-1H-[1,2,3]triazole-4-carboxamide

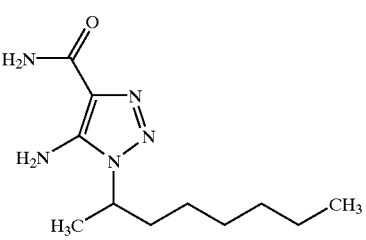

A solution of 23 g (135.9 mmol) of 3-azidononane and 17.14 g (203.8 mmol) of cyanacetamide in 80 ml of DMSO is admixed with a solution of 3.25 g (141 mmol) of sodium in 80 ml of ethanol. The reaction mixture is stirred at room temperature for 15 h and poured into 650 ml of ice-water. The pH is adjusted to pH 2 using 1N HCl and the precipitated solid is filtered off with suction, washed with water and dried under reduced pressure. This gives 17.40 (50%) of a slightly yellow solid.

200 MHz-$^1$H-NMR (CDCl$_3$, ppm): 6.81, s, broad, 1H; 5.50, s, broad, 1H; 5.01, s, broad, 2H; 3.91, quin., 1H; 1.92, m, 4H; 1.21, m, 8H; 0.86, m, 6H.

EXAMPLE XI

5-Amino-1-[1-(1-hydroxy-ethyl)-4-phenyl-butyl]-1H-[1,2,3]triazole-4-carboxamide

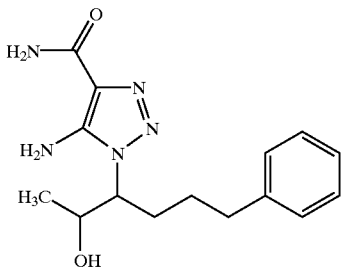

At 0° C., 1.19 g(18.3 mmol) of sodium azide in a mixture of 3 ml of water and 5 ml of dichloromethane are mixed dropwise with 1.046 g (mmol) of trifluoromethanesulphonic anhydride, and the resulting mixture is stirred at 0° C. for 2 hours. The phases are separated, the aqueous phase is extracted twice with dichloromethane and the combined organic phases are washed with saturated sodium bicarbonate solution. 386 mg (2 mmol) of 3-amino-6-phenyl-hexan-2-ol are dissolved in 2 ml of methanol and admixed successively with 10 mg of copper sulphate and 10 mg of potassium carbonate. The solution of the triflyl azide in dichloromethane is added and the mixture is made up to a total volume of 20 ml using dichloromethane. The mixture is stirred at room temperature for 15 hours, extracted with dilute ammonia solution and with EDTA solution, dried over sodium sulphate and concentrated using a rotary evaporator. This gives 331 mg of an oil which is dissolved in 1 ml of DMSO and admixed with a solution of 75 mg (3.5 mmol) of sodium in 1 ml of ethanol. 197 mg (2.34 mmol) of cyanoacetamide and, after 30 minutes, 2 ml of ethanol are added, and the mixture is stirred at room temperature for 15 hours. The mixture is poured into 30 ml of ice-water and, after addition of 3 ml of 1N HCl, extracted three times with dichloromethane and once with ethyl acetate. Chromatographic purification gives 72 mg (12%) of a foam.

200 MHz-$^1$H-NMR (CDCl$_3$, ppm, 2 diastereomers): 7.20, m, 5H; 5.69, s, broad, 1H; 5.48, s, broad, 2H; 5.36, s, broad, 1H; 4.24, m, 2H; 2.61, m, 2H; 2.31, m, 2H; 1.82, m, 2H; 1.55, m, 2H; 1.20, 2 d, 3H.

PREPARATION EXAMPLES

Example 1

5-(4-Methyl-benzyl)-3-(1-methyl-4-phenyl-butyl)-3,6-dihydro-[1,2,3]triazolo[4,5-d]pyrirnidin-7-one

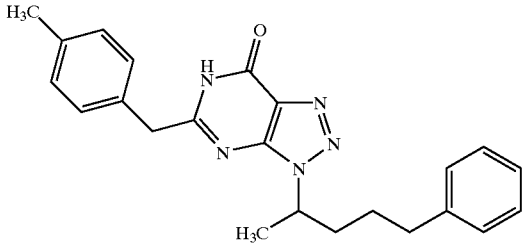

1.0 g (3.8 mmol) of 5-amino-1-(1-methyl-4-phenyl-butyl)-1H-[1,2,3]triazole-4-carboxamide are dissolved in a solution of 439 mg of sodium (19 mmol) in 38 ml of ethanol. 2.22 g (14.6 mmol) of methyl 4-methylphenylacetate are added, and the mixture is then refluxed overnight. The solvent is removed under reduced pressure, the residue is taken up with CH$_2$Cl$_2$, the organic phase is extracted twice with 1N HCl and dried over Na$_2$SO$_4$ and the solvent is removed under reduced pressure. Two chromatographic purifications (cyclohexane/ethyl acetate=3:1) give 853 mg (57%) of a solid.

M.p.: 130° C.

Example 2

3-(1-Methyl-4-phenyl-butyl)-5-pyridin-4-ylmethyl-3,6-dihydro-[1,2,3]triazolo[4,5-d]pyrimidin-7-one

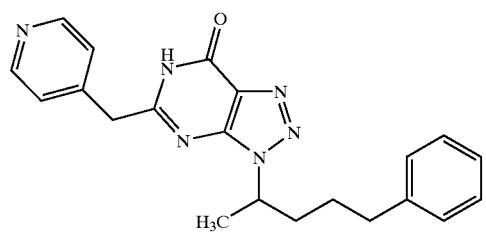

Analogously to the procedure of Example 1, the title compound is prepared from 1.0 g (3.8 mmol) of 5-amino-1-(1-methyl-4-phenyl-butyl)-1H-[1,2,3]triazole-4-carboxamide and 2.21 g (14.6 mmol) of methyl 4-pyridylacetate.

Yield: 266 mg (19%) of a foam; R$_f$=0.05 (cyclohexane/ethyl acetate=1:1).

Example 3

5-(4-Bromo-benzyl)-3-(1-methyl-4-phenyl-butyl)-3,6-dihydro-[1,2,3]triazolo[4,5-d]pyrimidin-7-one

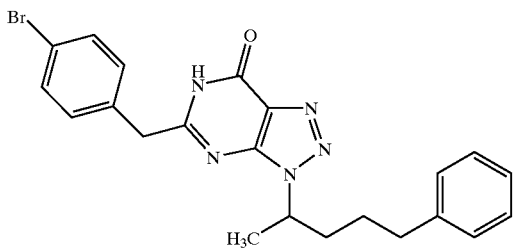

Analogously to the procedure of Example 1, the title compound is prepared from 1.0 g (3.8 mmol) of 5-amino-1-(1-methyl-4-phenyl-butyl)-1H-[1,2,3]triazole-4-carboxamide and 2.61 g (11.4 mmol) of methyl 4-bromophenylacetate.

Yield: 1.11 g (64%) of a yellow foam; R$_f$=0.59 (cyclohexane/ethyl acetate=1:2).

Example 4

5-Benzyl-3-(1-methyl-4-phenyl-butyl)-3,6-dihydro-[1,2,3]triazolo[4,5-d]pyrimidin-7-one

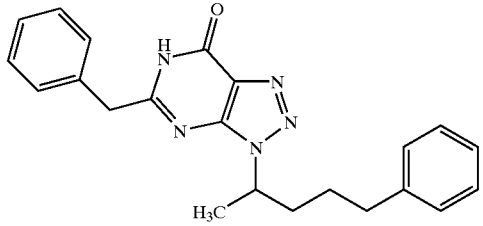

Analogously to the procedure of Example 1, the title compound is prepared from 566 mg (2 mmol) of 5-amino-1-(1-methyl-4-phenyl-butyl)-1H-[1,2,3]triazole-4-carboxamide and 1.16 g (7.7 mmol) of methyl phenylacetate.

Yield: 560 mg (75%) of a solid; M.p.: 112° C.

Example 5

5-(3,4-Dimethoxy-benzyl)-3-(1-methyl-4-phenyl-butyl)-3,6-dihydro-[1,2,3]triazolo-[4,5-d]pyrimidin-7-one

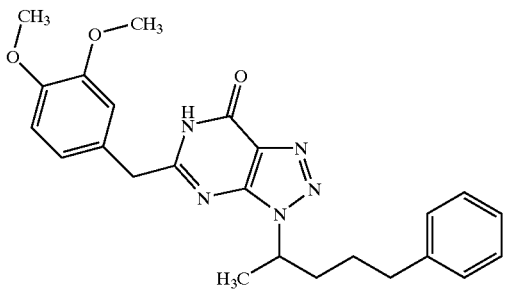

1.0 g (3.8 mmol) of 5-amino-1-(1-methyl-4-phenyl-butyl)-1H-[1,2,3]triazole-4-carboxamide, 2.13 g (19 mmol) of KOtBu and 2.09 g (9.94 mmol) of methyl 3,4-dimethoxyphenylacetate are dissolved in 40 ml of ethanol, and the mixture is refluxed for 15 h. The solvent is removed under reduced pressure, the residue is taken up in $CH_2Cl_2$ and the organic phase is extracted with 2N HCl. The organic phase is dried over $Na_2SO_4$ and the solvent is then removed under reduced pressure. Chromatographic purification (cyclohexane/ethyl acetate=1:1) gives 916 mg (56%) of a foam.

$R_f$=0.49 (cyclohexane/ethyl acetate=2:1).

Example 6

5-(4-Chloro-benzyl)-3-(1-methyl-4-phenyl-butyl)-3,6-dihydro-[1,2,3]triazolo[4,5-d]pyrimidin-7-one

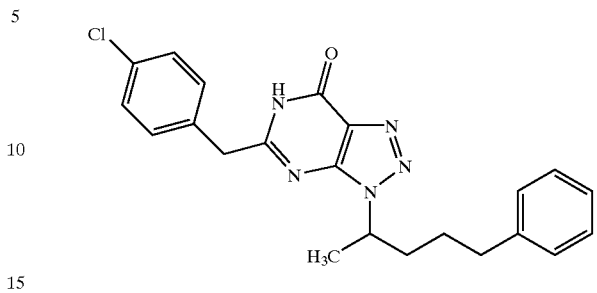

Analogously to the procedure of Example 5, the title compound is prepared from 1.0 g (3.8 mmol) of 5-amino-1-(1-methyl-4-phenyl-butyl)-1H-[1,2,3]triazole-4-carboxamide and 1.83 g (10.7 mmol) of methyl 4-chlorophenylacetate.

Yield: 921 mg(59%) of a white foam; $R_f$=0.58 (cyclohexane/ethyl acetate=4:1).

Example 7

5-(4-Methoxy-benzyl)-3-(1-methyl-4-phenyl-butyl)-3,6-dihydro-[1,2,3]triazolo[4,5-d]pyrimidin-7-one

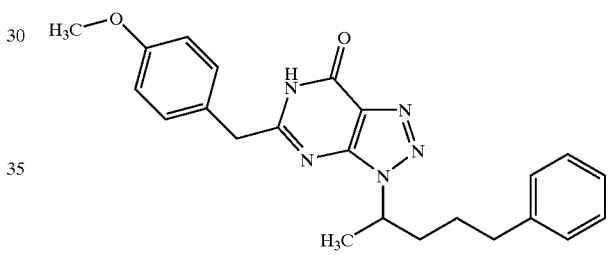

Analogously to the procedure of Example 5, the title compound is prepared from 1.0 g (3.8 mmol) of 5-amino-1-(1-methyl-4-phenyl-butyl)-1H-[1,2,3]triazole-4-carboxamide and 2.05 g (11.4 mmol) of methyl 4-methoxyphenylacetate.

Yield: 850 mg (55%) of a yellow foam; $R_f$=0.49 (cyclohexane/ethyl acetate=1:1).

Example 8

5-(3,4-Dichloro-benzyl)-3-(1-methyl-4-phenyl-butyl)-3,6-dihydro-[1,2,3]triazolo[4,5-d]pyrimidin-7-one

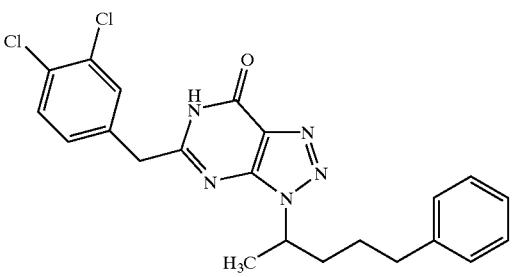

Analogously to the procedure of Example 5, the title compound is prepared from 1.0 g (3.8 mmol) of 5-amino- 1-(1-methyl-4-phenyl-butyl)-1H-[1,2,3]triazole-4-carboxamide and 2.5 g (11.4 mmol) of methyl 3,4-dichlorophenylacetate.

Yield: 1.08 g (64%) of a white foam; $R_f$=0.48 (cyclohexane/ethyl acetate=4:1).

Example 9

5-Biphenyl-4-ylmethyl-3-(1-methyl-4-phenyl-butyl)-3,6-dihydro-[1,2,3]triazolo[4,5-d]pyrimidin-7-one

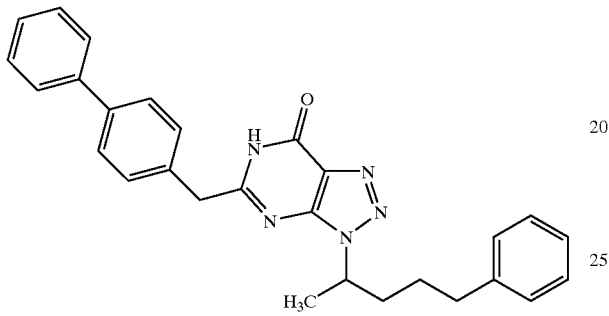

Analogously to the procedure of Example 5, the title compound is prepared from 1.0 g (3.8 mmol) of 5-amino-1-(1-methyl-4-phenyl-butyl)-1H-[1,2,3]triazole-4-carboxamide and 2.58 g (11.4 mmol) of methyl biphenylacetate.

Yield: 1.03 g (64%) of a white foam; $R_f$=0.68 (cyclohexane/ethyl acetate=4:1).

Example 10

5-(4-Amino-benzyl)-3-(1-methyl-4-phenyl-butyl)-3,6-dihydro-[1,2,3]triazolo[4,5-d]pyrimidin-7-one

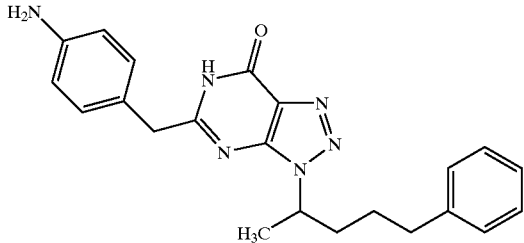

Analogously to the procedure of Example 5, the title compound is prepared from 1.0 g (3.8 mmol) of 5-amino-1-(1-methyl-4-phenyl-butyl)-1H-[1,2,3]triazole-4-carboxamide and 1.88 g (11.4 mmol) of 4-aminophenylacetic acid.

Yield: 600 mg (39%) of a yellow foam; $R_f$=0.59 (cyclohexane/ethyl acetate=1:4).

Example 11

5-(Hydroxy-phenyl-methyl)-3-(1-methyl-4-phenyl-butyl)-3,6-dihydro-[1,2,3]triazolo-[4,5-d]pyrimidin-7-one

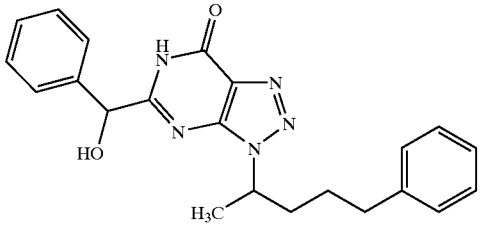

Analogously to the procedure of Example 5, the title compound is prepared from 1.0 g (3.8 mmol) of 5-amino-1-(1-methyl-4-phenyl-butyl)-1H-[1,2,3]triazole-4-carboxamide and 1.89 g (11.4 mmol) of methyl mandelate.

Yield: 512 mg (34%) of a white foam; $R_f$=0.63 (cyclohexane/ethyl acetate=1:4).

Example 12

5-(4-Fluoro-benzyl)-3-(1-methyl-4-phenyl-butyl)-3,6-dihydro-[1,2,3]triazolo[4,5-d]pyrimidin-7-one

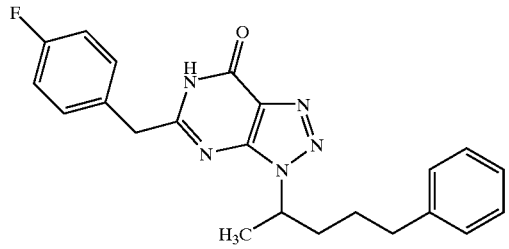

Analogously to the procecure of Example 5, the title compound is prepared from 1.0 g (3.8 mmol) of 5-amino-1-(1-methyl-4-phenyl-butyl)-1H-[1,2,3]triazole-4-carboxamide and 1.92 g (11.4 mmol) of methyl 4-fluorophenylacetate.

Yield: 990 mg (67%) of a yellow foam; $R_f$=0.69 (CH/EA=1:2).

Example 13

5-(4-Dimethylamino-benzyl)-3-(1-methyl-4-phenyl-butyl)-3,6-dihydro-[1,2,3]triazolo[4,5-d]pyrimidin-7-one

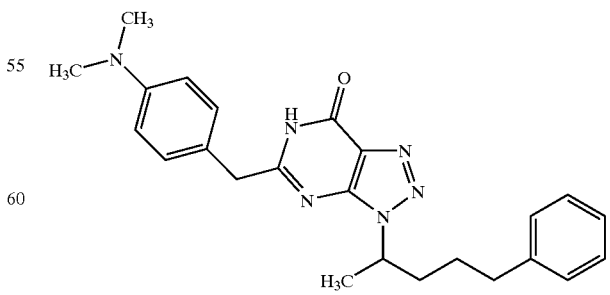

Analogously to the procedure of Example 5, the title compound is prepared from 1.0 g (3.8 mmol) of 5-amino- 1-(1-methyl-4-phenyl-butyl)-1H-[1,2,3]triazole-4-carboxamide and 1.77 g (9.15 mmol) of methyl 4-dimethylaminophenylacetate.

Yield: 620 mg (41%) of a yellow foam; $R_f$=0.75 (cyclohexane/ethyl acetate=1:4).

Example 14

5-Benzo[1,3]dioxol-5-ylmethyl-3-[1-methyl-4-phenyl-butyl]-3,6-dihydro-[1,2,3]triazolo[4,5-d]pyrimidin-7-one

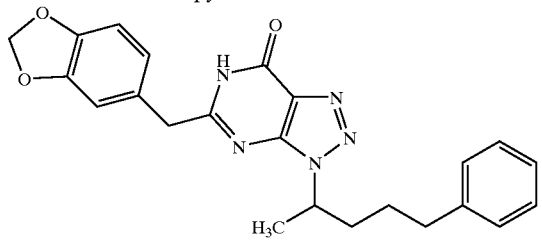

Analogously to the procedure of Example 5, the title compound is prepared from 18 mg (0.066 mmol) of 5-amino-1-(1-methyl-4-phenyl-butyl)-1H-[1,2,3]triazole-4-carboxamide and 40.8 g (0.21 mmol) of methyl 3,4-methylenedioxyphenylacetate.

Yield: 22 mg (80%) of a solid; $R_f$=0.31 (dichloromethane/methanol=95:5).

Example 15

N-{4-[3-(1-Methyl-4-phenyl-butyl)-7-oxo-6,7-dihydro-3H-[1,2,3]triazolo[4,5-d]pyrimidin-5-ylmethyl]-phenyl}-acetamide

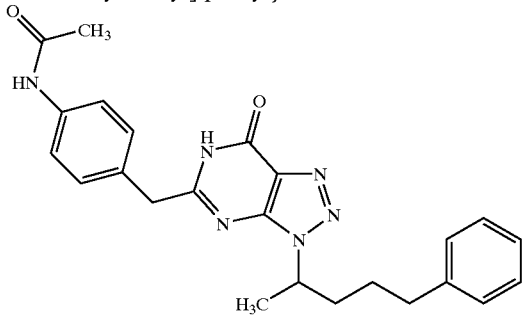

650 mg (1.62 mmol) of 5-(4-amino-benzyl)-3-(1-methyl-4-phenyl-butyl)-3,6-dihydro-[1,2,3]-triazolo-[4,5-d]pyrimidin-7-one are suspended in 10 ml of dichloromethane, and the mixture is cooled to 0° C. 0.45 ml (3.24 mmol) of triethylamine, 0.23 ml (3.24 mmol) of acetyl chloride and a spatula tip of DMAP are added successively, and the reaction mixture is stirred at room temperature for 3 hours. The mixture is diluted with 100 ml of dichloromethane and the organic phase is washed with saturated sodium bicarbonate solution, saturated ammonium chloride solution and water and then dried over sodium sulphate. Two chromatographic purifications give 82 mg (11.5%) of a white foam.

$R_f$=0.09 (cyclohexane/ethyl acetate=1:2).

Example 16

5-Benzoyl-3-(1-methyl-4-phenyl-butyl)-3,6-dihydro-[1,2,3]triazolo[4,5-d]pyrimidin-7-one

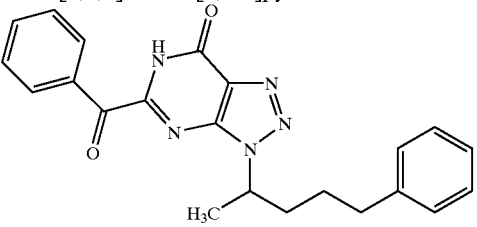

384 mg (0.988 mmol) of 5-(hydroxy-phenyl-methyl)-3-(1-methyl-4-phenyl-butyl)-3,6-dihydro-[1,2,3]triazolo[4,5-d]pyrimidin-7-one are dissolved in a mixture of 3 ml of DMSO and 10 ml of dichloromethane, and the solution is cooled to 0° C. 1.37 ml (9.88 mmol) of triethylamine and 692 mg (4.35 mmol) of pyridine-$SO_3$ complex are added, and the reaction mixture is then stirred at room temperature for 15 hours. For work-up, the mixture is diluted with 100 ml of dichloromethane and the organic phase is washed with 1N HCl and saturated sodium bicarbonate solution and then dried over sodium sulphate. The solvent is removed, and chromatographic purification gives 185 mg (48%) of a solid, m.p.: 105° C.

Example 17 and Example 18

3-(1-Methyl-4-phenyl-butyl)-5-[4-(morpholine-4-sulphonyl)-benzyl]-3,6-dihydro-[1,2,3]triazolo-[4,5-d]pyrimidin-7-one (Example 17) and 3-(1-Methyl-4-phenyl-butyl)-5-[3-(morpholine-4-sulphonyl)-benzyl]-3,6-dihydro[1,2,3]triazolo[4,5-d]pyrimidin-7-one (Example 18)

(Example 17)

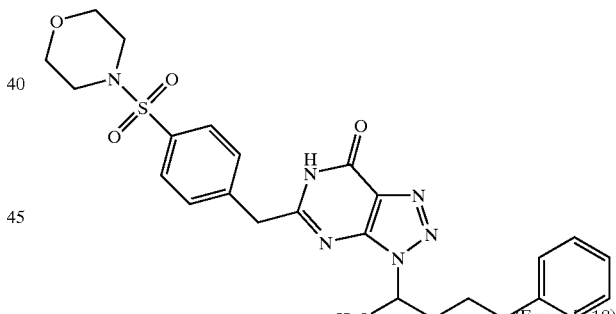

(Example 18)

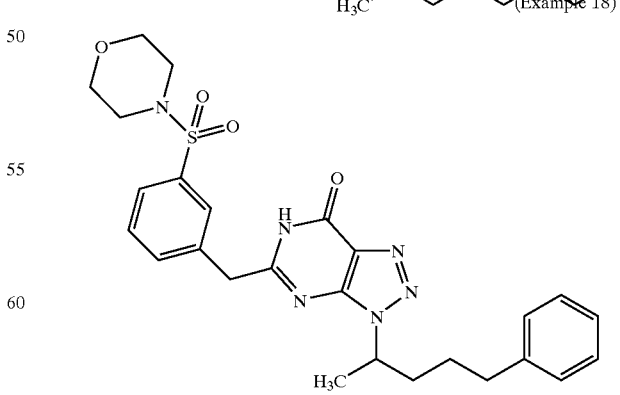

0.75 g (2.74 mmol) of 5-amino-1-(1-methyl-4-phenyl-butyl)-1H-[1,2,3]triazole-4-carboxamide and a solution of 1.92 g (6.13 mmol) of methyl 4-morpholinosulphonylphenylacetate in 2 ml of ethanol are added to a solution of 1.54 g (13.7 mmol) of KOtBu in 20 ml of ethanol. The reaction mixture is refluxed for 15 hours and the solvent is removed under reduced pressure. The residue is neutralized with 1N HCl and taken up in dichloromethane. The organic phase is washed with ammonium chloride solution and water and dried over sodium sulphate. Chromatographic purification and separation of the regioisomers gives 334 mg (23%) of the compound of Example 17 and 186 mg (13%) of the compound of Example 18.

Example 17: 200 MHz-1H-NMR (CDCl$_3$, ppm): 12.8, s, broad, 1H; 7.68, s, broad, 4H; 7.19, m, 5H; 5.00, m, 1H; 4.22, s, 2H; 3.70, m, 4H; 2.95, m, 4H; 2.60, dt, 2H; 2.23, m, 1H; 2.00, m, 1H; 1.69, d, 3H; 1.56, m, 2H.

Example 18: 200 MHz-1H-NMR (CDCl$_3$, ppm): 12.81, s, broad, 1H; 7.90, s, 1H; 7.80, m, 2H; 7.50, m, 1H; 7.10, m, 5H; 4.98, m, 1H; 4.27, s, 2H; 3.68, m, 4H; 2.98, m, 2H; 2.60, m, 2H; 2.20, m, 1H; 1.98, m, 2H; 1.68, d, 3H; 1.48, m, 2H.

Example 19 and Example 20

N-Methyl-4-[3-(1-methyl-4-phenyl-butyl)-7-oxo-6,7-dihydro-3H-[1,2,3]-triazolo-[4,5-d]pyrimidin-5-ylmethyl]-benzenesulphonamide (Example 19) and N-Methyl-3-[3-(1-methyl-4-phenyl-butyl)-7-oxo-6,7-dihydro-3H-[1,2,3]-triazolo-[4,5-d]pyrimidin-5-ylmethyl]-benzenesulphonamide (Example 20)

(Example 19)

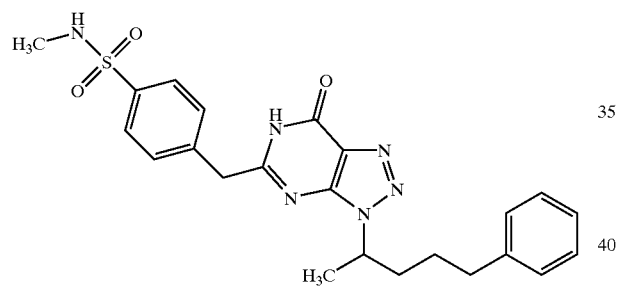

(Example 20)

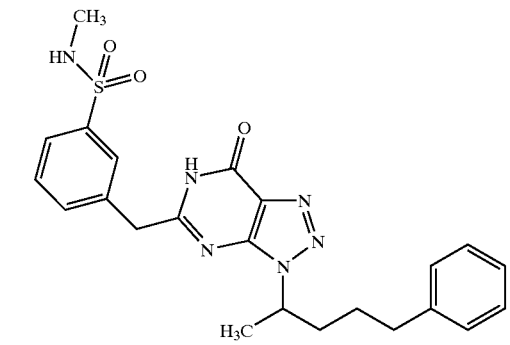

Analogously to the procedure for Examples 17 and 18, the title compounds are prepared from 0.75 g of 5-amino-1-(1-methyl-4-phenyl-butyl)-1H-[1,2,3]triazole-4-carboxamide and 1.58 g (6.14 mmol) of methyl 4-(N-methylsulphonylamide)-phenylacetate.

(Example 19) yield: 269 mg (21%), m.p.: 69° C. and (Example 20) yield: 100 mg (7.8%), m.p.:57° C.

Example 21 and Example 22

N-(2-Dimethylamino-ethyl)-4-[3-(1-methyl-4-phenyl-butyl)-7-oxo-6,7-dihydro-3H-[1,2,3]triazolo[4,5-d]pyrimidin-5-ylmethyl]benzenesulphonamide (Example 21) and N-(2-Dimethylamino-ethyl)-3-[3-(1-methyl-4-phenyl-butyl)-7-oxo-6,7-dihydro-3H-[1,2,3]triazolo [4,5-d]pyrimidin-5-ylmethyl] benzenesulphonamide (Example 22)

(Example 21)

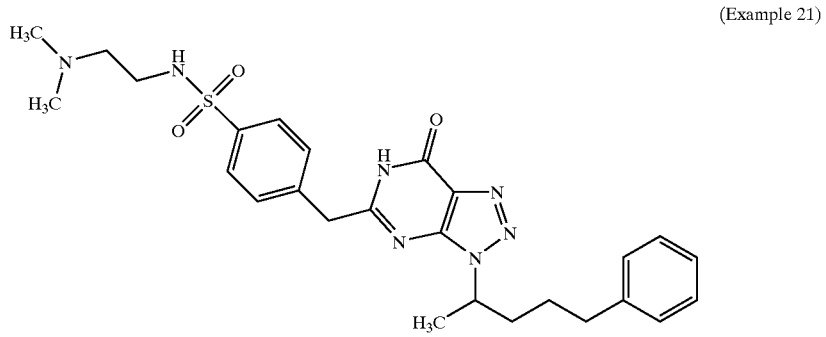

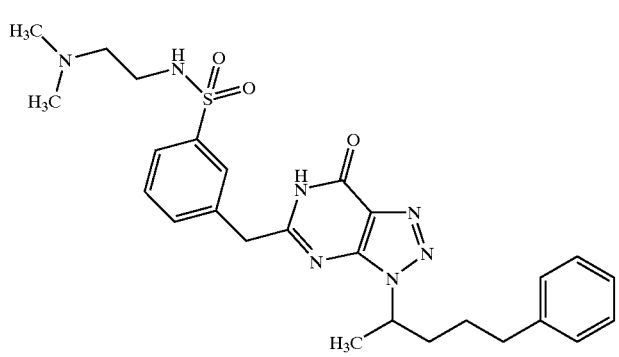

(Example 22)

Analogously to the procedure for Examples 17 and 18, the title compounds are prepared from 0.75 g of 5-amino-1-(1-methyl-4-phenyl-butyl)-1H-[1,2,3]triazole-4-carboxamide and 1.89 g (6.01 mmol) of methyl 4-(N-2-dimethylaminoethylsulphonylamide)-phenylacetate.

(Example 21): yield: 204 mg (14%) and (Example 22): yield: 109 mg (7.6%), $R_f$=0.05 (cyclohexane/ethyl acetate=1:1).

Example 23 and Example 24

N-(2-Hydroxyethyl)-4-[3-(1-methyl-4-phenyl-butyl)-7-oxo-6,7-dihydro-3H-[1,2,3]triazolo[4,5-d]pyrimidin-5-ylmethyl]benzenesulphonamide (Example 23) and N-(2-Hydroxyethyl)-3-[3-(1-methyl-4-phenyl-butyl)-7-oxo-6,7-dihydro-3H-[1,2,3]triazolo[4,5-d]pyrimidin-5-ylmethyl]benzenesulphonamide (Example 24)

(Example 23)

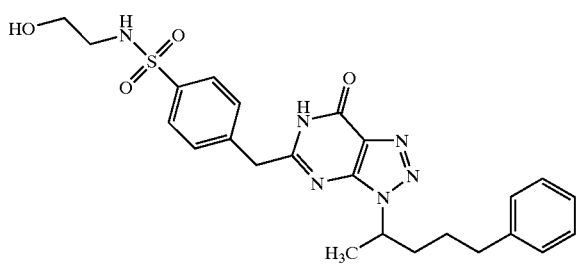

(Example 24)

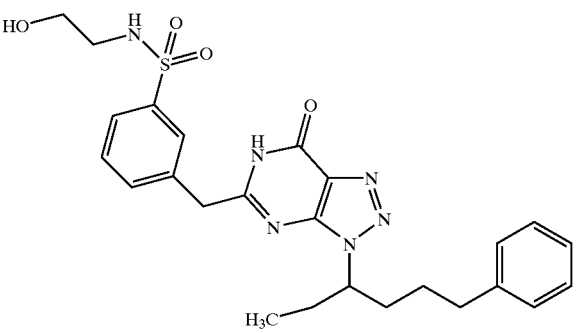

Analogously to the procedure for Examples 17 and 18, the title compounds are prepared from 0.75 g of 5-amino-1-(1-methyl-4-phenyl-butyl)-1H-[1,2,3]triazole-4-carboxamide and 1.97 g (6.85 mmol) of methyl 4-(N-2-hydroxyethylsulphonylamide)-phenylacetate.

(Example 23) yield: 266 mg (20%) $R_f$=0.13 (cyclohexane/ethyl acetate=1:1) and (Example 24): yield: 108 mg (8%) $R_f$=0.07 (cyclohexane/ethyl acetate=1:1).

Example 25 and Example 26

Ethyl 1-{4-[3-(1-methyl-4-phenyl-butyl)-7-oxo-6,7-dihydro-3H-[1,2,3]triazol[4,5-d]pyrimidin-5-ylmethyl]benzenesulphonyl}-piperidinecarboxylate (Example 25) and Ethyl 1-{3-[3-(1-methyl-4-phenyl-butyl)-7-oxo-6,7-dihydro-3H-[1,2,3]triazolo[4,5-d]pymidin-5-ylmethyl]benzenesulphonyl}-piperidinecarboxylate (Example 26)

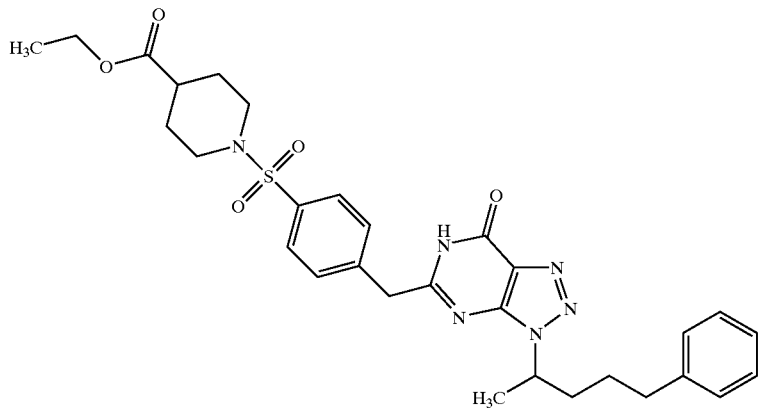
(Example 25)

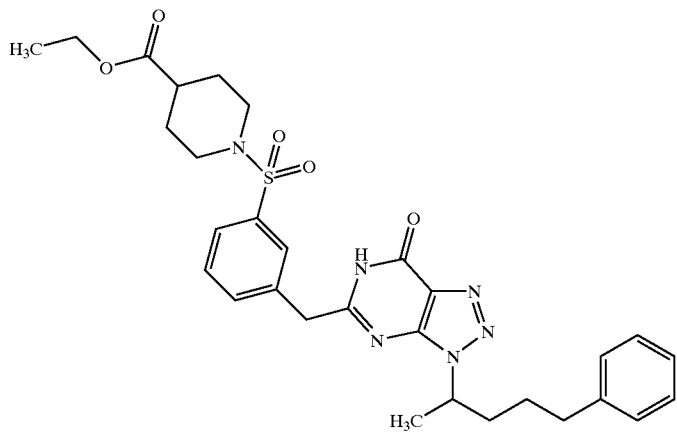
(Example 26)

Analogously to the procedure for Examples 17 and 18, the title compounds are prepared from 0.75 g of 5-amino-1-(1-methyl-4-phenyl-butyl)-1H-[1,2,3]triazole-4-carboxamide and 2.40 g (5.85 mmol) of tert-butyl N-(ethyl 4-sulphonylphenylacetate)-piperidinecarboxylate.

(Example 25) yield: 111 mg (7%); 200 MHz-1H-NMR (CDCl$_3$, ppm): 12.63, s, broad, 1H; 7.62, AB, 4H; 7.20, m, 5H; 5.00, m, 1H; 4.21, s, 2H; 4.10, q, 2H; 3.60, m, 2H; 2.60, m, 2H; 2.48, m, 2H; 2.22, m, 2H; 1.90, m, 5H; 1.68, d, 3H; 1.60, m, 2H; 1.20, t, 2H; and.

(Example 26) yield: 43 mg (3%); 200 MHz-1H-NMR (CDCl$_3$, ppm): 11.97, s, broad, 1H; 7.99, s, 1H; 7.67, m, 2H; 7.48, m, 1H; 7.18, m, 5H; 4.98, m, 1H; 4.22, s, 2H; 4.10, quart., 2H; 3.61, m, 2H; 2.55, m, 4H; 2.20, m, 2H; 1.90, m, 5H; 1.71, t, 3H; 1.68, d, 3H; 1.55, m, 2H.

Example 27

3-(1-Methyl-4-phenyl-butyl)-5-[4-(4-methyl-piperazine-1-sulphonyl)-benzyl]-3,6-dihydro-[1,2,3]triazolo[4,5-d]pyrimidin-7-one

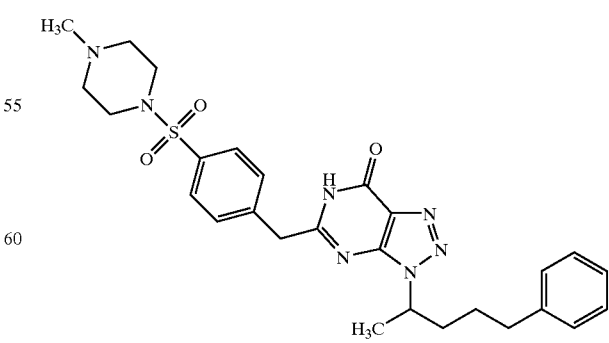

Analogously to the procedure of Examples 17 and 18, the title compound is prepared from 0.75 g of 5-amino-1-(1- methyl-4-phenyl-butyl)-1H-[1,2,3]triazole-4-carboxamide and 1.97 g (6.85 mmol) of methyl 4-(N-2-hydroxyethylsulphonylamide)-phenylacetate.

Yield: 278 mg (19%), $R_f$=0.18 (cyclohexane/ethyl acetate=1:1).

Example 28

5-Benzo[1,3]dioxol-5-ylmethyl-3-[1-ethyl-heptyl]-3,6-dihydro-[1,2,3]triazolo[4,5-d]pyrimidin-7-one

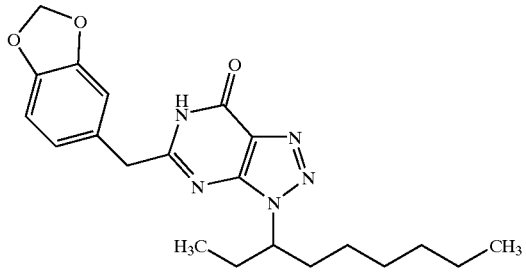

18 mg (0.071 mmol) of 5-amino-1-(1-methyl-heptyl)-1H-[1,2,3]triazole-4-carboxamide and 40.8 mg (0.21 mmol) of methyl 3,4-methylenedioxyphenylacetate in 1.06 ml of a 0.5 M ethanolic potassium tert-butoxide solution are heated under reflux for 6 hours. The mixture is diluted with dichloromethane and saturated sodium bicarbonate solution. Chromatographic purification gives 23 mg (81%) of a solid, $R_f$=0.42 (dichloromethane/ methanol=95:5).

Example 29

5-(4-Bromo-benzyl)-3-[1-(1-hydroxy-ethyl)-4-phenyl-butyl]-3,6-dihydro-[1,2,3]triazolo[4,5-d]pyrimidin-7-one

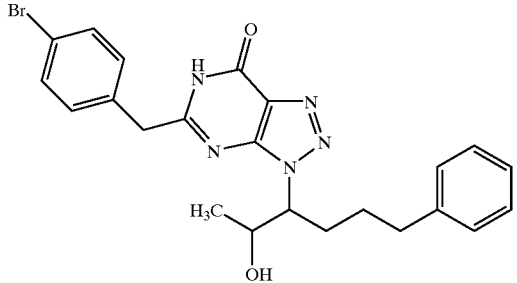

10 mg (0.024 mmol) of 5-amino-1-[1-(1-hydroxy-ethyl)-4-phenyl-butyl]-1H-[1,2,3]-triazole-4-carboxamide, 20 mg of potassium tert-butoxide (0.166 mmol) and 20 mg (0.107 mmol) of methyl 4-bromo-phenylacetate in 0.3 ml of ethanol are heated under reflux for 15 hours. The mixture is diluted with dichloromethane and sodium bicarbonate solution. Chromatographic purification gives 8 mg (66%) of a solid, $R_f$=0.46 (dichloromethane/methanol=15:1).

Example 30

5-Benzo[1,3]dioxol-5-ylmethyl-3-[1-(1-hydroxy-ethyl)-4-phenyl-butyl]-3,6-dihydro-[1,2,3]triazolo[4,5-d]pyrimidin-7-one

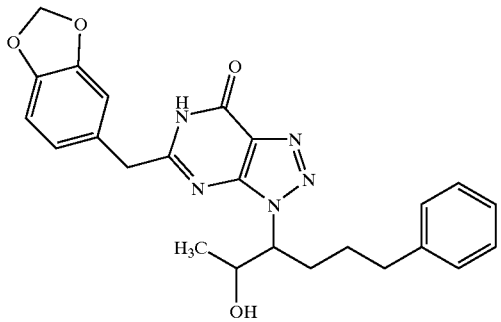

Analogously to the procedure of Example 29, the title compound is prepared from 10 mg (0.024 mmol) of 5-amino-1-[1-(1-hydroxy-ethyl)-4-phenyl-butyl]-1H-[1,2,3]triazole-4-carboxamide and 20 mg (0.107 mmol) of methyl 3,4-methylenedioxyphenylacetate.

Yield: 7 mg (63%); $R_f$=0.46 (dichloromethane/methanol=15:1).

Example 31

5-(3,4-Dimethoxy-benzyl)-3-[1-(1-hydroxy-ethyl)-4-phenyl-butyl]-3,6-dihydro-[1,2,3]triazolo[4,5-d]pyrimidin-7-one

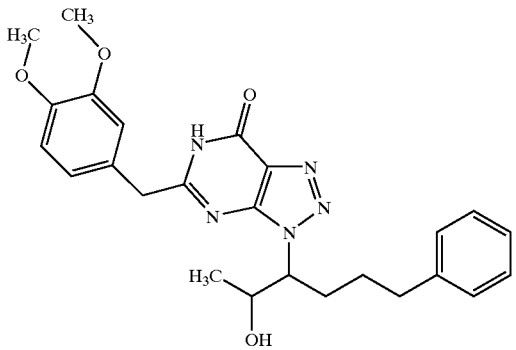

Analogously to the procedure of Example 29, the title compound is prepared from 10 mg (0.024 mmol) of 5-amino-1-[1-(1-hydroxy-ethyl)-4-phenyl-butyl]- 1H-[1,2,3]triazole-4-carboxamide and 20 mg (0.107 mmol) of methyl 3,4-dimethoxyphenylacetate.

Yield: 7 mg (63%); $R_f$=0.46 (dichloromethane/methanol=15:1).

Example 32

5-(3,4,5-Trimethoxy-benzyl)-3-[1-(1-hydroxy-ethyl)-4-phenyl-butyl]-3,6-dihydro-[1,2,3]triazolo[4,5-d]pyrimidin-7-one

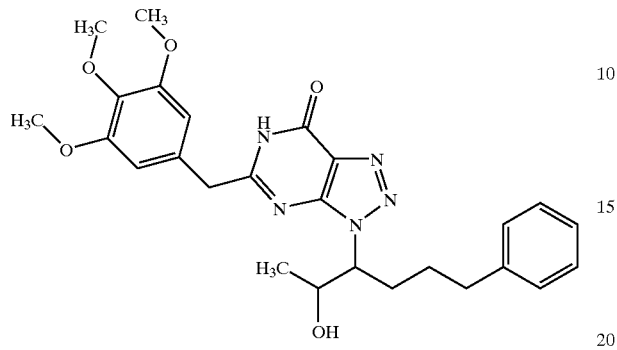

Analogously to the procedure of Example XI, the title compound is prepared from 10 mg (0.024 mmol) of 5-amino-1-[1-(1-hydroxy-ethyl)-4-phenyl-butyl]-1H-[1,2,3]triazole-4-carboxamide and 20 mg (0.107 mmol) of methyl 3,4,5-trimethoxyphenylacetate.

Yield: 7 mg (63%); $R_f$=0.44 (dichloromethane/methanol=15:1).

Example 33

3-[1-(1-Hydroxy-ethyl)-4-phenyl-butyl]-5-[4-(morpholine-4-sulphonyl)-benzyl]-3,6-dihydro-[1,2,3]triazolo[4,5-d]pyrimidin-7-one

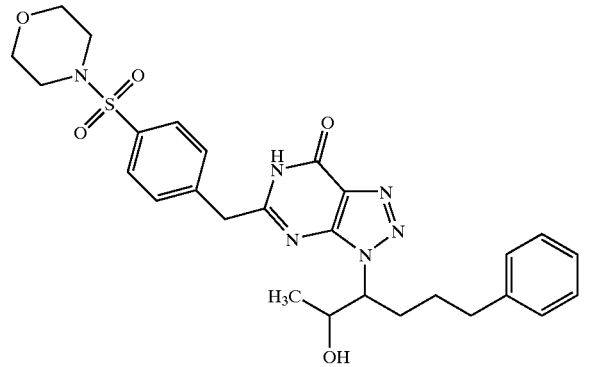

Analogously to the procedure of Example 29, the title compound is prepared from 10 mg (0.024 mmol) of 5-amino-1-[1-(1-hydroxy-ethyl)-4-phenyl-butyl]-1H-[1,2,3]triazole-4-carboxamide and 30 mg (0.107 mmol) of methyl 4-morpholinosulphonylphenylacetate.

Yield: 10 mg (75%); $R_f$=0.37 (dichloromethane/methanol=15:1).

What is claimed is:

1. Dihydro-[1,2,3]triazolo-[4,5-d]pyrimidin-7-ones of the general formula (I)

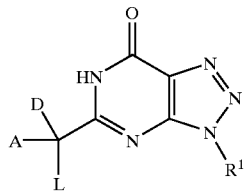

(I)

in which
$R^1$ represents cycloalkyl having 3 to 8 carbon atoms, or represents a radical of the formula

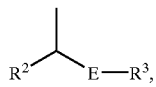

in which
$R^2$ represents straight-chain or branched alkyl having up to 10 carbon atoms which is optionally substituted by hydroxyl,
E represents a radical of the formula —CH$_2$—T,
in which
T represents a straight-chain or branched alkylene chain having up to 10 carbon atoms,
$R^3$ represents hydrogen or aryl having 6 to 10 carbon atoms which is optionally substituted up to 3 times by identical or different substitutents from the group consisting of halogen, hydroxyl, nitro, trifluoromethyl and straight-chain or branched alkyl or alkoxy having in each case up to 6 carbon atoms,
A and D represent hydrogen,
or
A represents hydrogen
and
D represents hydroxyl,
or
A and D together represent a radical of the formula =O,
L represents a radical of the formula

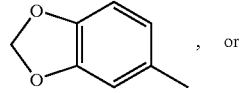, or represents aryl having 6 to 10 carbon atoms or represents a 5- to 7-membered aromatic, optionally benzo-fused heterocycle having up to 3 heteroatoms from the group consisting of S, N and/or O, where the ring systems listed above under L are substituted up to 3 times by one or more identical or different of the following substituents: halogen, hydroxyl, nitro, trifluoromethyl, carboxyl, straight-chain or branched alkyl, alkoxy and alkoxycarbonyl having in each case up to 6 carbon atoms, a radical of the formula —(V)$_a$—NR$^4$R$^5$,
in which
a represents a number 0 or 1,
V represents a radical of the formula —CO or —SO$_2$,
$R^4$ and $R^5$ are identical or different and represent hydrogen or straight-chain or branched acyl or alkoxycarbonyl having in each case up to 6 carbon atoms, or represent straight-chain or branched alkyl having up to 6 carbon atoms which is optionally substituted by hydroxyl, amino or by straight-chain or branched alkyl- or dialkylamino having in each case up to 6 carbon atoms, or R⁴ and R⁵ together with the nitrogen atom form a 5- or 6-membered saturated heterocycle which may optionally contain a further heteroatom from the group consisting of S and O or a radical of the formula —NR⁶ and which is optionally substituted by straight-chain or branched alkoxycarbonyl having up to 6 carbon atoms, in which R⁶ represents hydrogen or straight-chain or branched alkyl having up to 4 carbon atoms, and/or the ring systems listed under L are optionally substituted by aryl having 6 to 10 carbon atoms and a 5- to 7-membered aromatic, optionally benzo-fused heterocycle having up to 3 heteroatoms from the group consisting of S, N and O, where these ring systems for their part are optionally substituted up to 2 times by identical or different substituents from the group consisting of halogen, hydroxyl, nitro, carboxyl, trifluoromethyl and straight-chain or branched alkyl, alkoxy, or alkoxycarbonyl having in each case up to 5 carbon atoms, or by a group of the formula —(V')$_b$—NR⁷R⁸, in which b has the meaning of a given above and is identical to or different from this meaning, R⁷ and R⁸ have the meanings of R⁴ and R⁵ given above and are identical to or different from these meanings, V' has the meaning of V given above and is identical to or different from this meaning, and their tautomers and salts.

2. Dihydro-[1,2,3]triazolo-[4,5-d]pyrimidin-7-ones according to claim 1, characterized in that R¹ represents cyclopropyl, cyclobutyl, cyclopentyl, cyclohexyl or cycloheptyl, or represents a radical of the formula

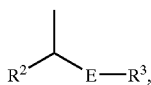

in which

R² represents straight-chain or branched alkyl having up to 8 carbon atoms which is optionally substituted by hydroxyl, and E represents a radical of the formula —CH₂—T—, in which T represents a straight-chain or branched alkylene chain having up to 8 carbon atoms, R³ represents hydrogen or phenyl which is optionally substituted up to 2 times by identical or different substituents from the group consisting of fluorine, chlorine, bromine, hydroxyl, nitro, trifluoromethyl and straight-chain or branched alkyl or alkoxy having in each case up to 5 carbon atoms, A and D represent hydrogen, or A represents hydrogen and D represents hydroxyl, or A and D together represent a radical of the formula =O, L represents a radical of the formula

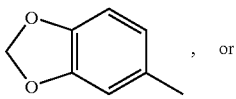

represents phenyl, naphthyl, pyridyl, thienyl, indolyl or furyl, which are optionally substituted up to 3 times by identical or different substituents selected from the group consisting of fluorine, chlorine, bromine, trifluoromethyl, hydroxyl, nitro, carboxyl, straight-chain or branched alkyl, alkoxy and alkoxycarbonyl having in each case up to 5 carbon atoms and/or by a radical of the formula —(V)$_a$NR⁴R⁵, in which a represents a number 0 or 1, V represents a radical of the formula —CO or —SO₂, R⁴ and R⁵ are identical or different and represent hydrogen or straight-chain or branched acyl or alkoxycarbonyl having in each case up to 4 carbon atoms, or represent straight-chain or branched alkyl having in each case up to 5 carbon atoms which is optionally substituted by hydroxyl, amino or by straight-chain or branced alkyl- or dialkylamino having in each case up to 5 carbon atoms, or R⁴ and R⁵ together with the nitrogen atom form a morpholinyl, piperidinyl or piperazinyl ring which is optionally substituted via a nitrogen atom by straight-chain or branched alkyl having up to 3 carbon atoms, which rings are optionally substituted by straight-chain or branched alkoxycarbonyl having up to 4 carbon atoms, and/or the ring systems listed under L are optionally substituted by naphthyl, phenyl, pyridyl, indolyl, thienyl and furyl which are optionally substituted by fluorine, chlorine, bromine, hydroxyl, nitro, carboxyl, trifluoromethyl or by straight-chain or branched alkyl, alkoxy or alkoxycarbonyl having in each case up to 3 carbon atoms or by a group of the formula —(V')$_b$NR⁷R⁸, in which b has the meaning of a given above and is identical to or different from this meaning, V' has the meaning of V given above and is identical to or different from this meaning, R⁷ and R⁸ have the meanings of R⁴ and R⁵ given above, and their tautomers and salts.

3. Dihydro-[1,2,3]triazolo-[4,5-d]pyrimidin-7-ones according to claim 1 or 2, characterized in that R¹ represents cyclopropyl, cyclobutyl, cyclopentyl, cyclohexyl or cycloheptyl, or represents a radical of the formula

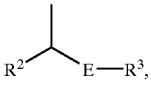

in which

R² represents straight-chain or branched alkyl having up to 7 carbon atoms which is optionally substituted by hydroxyl, and E represents a radical of the formula —CH$_2$—T—,
in which
T represents a straight-chain or branched alkylene chain having up to 7 carbon atoms,
R$^3$ represents hydrogen or phenyl which is optionally substituted up to 2 times by identical or different substituents from the group consisting of fluorine, chlorine, bromine, hydroxyl, nitro, trifluoromethyl and straight-chain or branched alkyl or alkoxy having in each case up to 4 carbon atoms, A and D represent hydrogen,
or
A represents hydrogen
and
D represents hydroxyl,
or
A and D together represent a radical of the formula =O,
L represents a radical of the formula

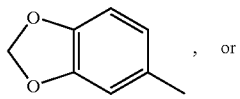, or represents phenyl or pyridyl which are optionally substituted up to 3 times by identical or different substituents selected from the group consisting of fluorine, chlorine, bromine, trifluoromethyl, hydroxyl, nitro, carboxyl, straight-chain or branched alkyl, alkoxy and alkoxycarbonyl having in each case up to 4 carbon atoms and/or by a radical of the formula —(V)$_a$NR$^4$R$^5$,
in which
a represents a number 0 or 1,
V represents a radical of the formula —CO or —SO$_2$,
R$^4$ and R$^5$ are identical or different and represent hydrogen or straight-chain or branched acyl or alkoxycarbonyl having in each case up to 3 carbon atoms, or
represent straight-chain or branched alkyl having in each case up to 4 carbon atoms which is optionally substituted by hydroxyl, amino or by straight-chain or branched alkyl- or dialkylamino having in each case up to 3 carbon atoms,
or
R$^4$ and R$^5$ together with the nitrogen atom form a morpholinyl, piperidinyl or piperazinyl ring which is optionally substituted via a nitrogen atom by straight-chain or branched alkyl having up to 3 carbon atoms, which rings are optionally substituted by straight-chain or branched alkoxycarbonyl having up to 4 carbon atoms,
and/or the ring systems listed under L are optionally substituted by phenyl or pyridyl,
and their tautomers and salts.

4. Process for preparing the dihydro-[1,2,3]triazolo-[4,5-d]pyrimidin-7-ones according to claim 1, characterized in that, if A and D represent hydrogen, compounds of the general formula (II),

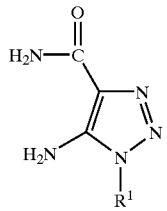

(II)

in which
R$^1$ is as defined above in claim 1
are reacted with compounds of the general formula (III)

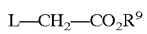 (III)

in which
L is as defined above in claim 1
and
R$^9$ represents C$_1$–C$_4$-alkyl,
in inert solvents,
and the substituents listed under the substituents R$^1$, R$^3$ and L are introduced or derivatized by subsequent reactions.

5. Medicaments, comprising one or more dihydro-[1,2,3]triazolo-[4,5-d]pyrimidin-7-ones according to claim 1 and an auxiliary or excipient.

6. A method of treating cardiovascular disorders, thromboembolic disorders and ischaemias, and urogenital system disorders, comprising administering to a mammal an effective amount of a compound according to claim 1.

7. The process of claim 4, wherein said subsequent reaction is selected from acylation, oxidation, substitution and reduction.

8. The method of claim 6, wherein said cardiovascular disorder is selected from hypertension, neuronal hypertension, stable and unstable angina, peripheral disorders, and arrhythmias.

9. The method of claim 6, wherein said thromboembolic disorders and ischaemias are selected from myocardial infarction, stroke, transistory and ischaemic attacks, angina pectoris, obstruction of peripheral circulation, restenoses after thrombolysis therapy, percutaneous transluminal angioplasty (PTA), percutaneous transluminal coronary angioplasties (PTCA) and bypass.

10. The method of claim 6, wherein said disorder of the urogenital system is selected from hypertrophy of the prostate, incontinence, erectile dysfunction and female sexual dysfunction.

* * * * *